United States Patent [19]

Kamishita

[11] Patent Number: 4,545,992

[45] Date of Patent: Oct. 8, 1985

[54] PHARMACEUTICAL PREPARATIONS

[75] Inventor: Takuzo Kamishita, Takatsuki, Japan

[73] Assignee: Toko Yakuhin Industry Co., Ltd., Osaka, Japan

[21] Appl. No.: 401,707

[22] Filed: Jul. 26, 1982

[30] Foreign Application Priority Data

Aug. 14, 1981 [JP]  Japan ................................ 56-128032

[51] Int. Cl.⁴ ..................... A61K 31/19; A61K 31/34; A61K 31/38; A61K 31/40; A61K 31/44; A61K 31/54; A61K 31/61; A61K 37/185; A61K 31/415

[52] U.S. Cl. ................................. 514/161; 424/195.1; 514/303; 514/570; 514/420; 514/969; 514/944

[58] Field of Search ........................ 424/234, 317, 232

[56] References Cited

U.S. PATENT DOCUMENTS

| | | | |
|---|---|---|---|
| 2,079,166 | 5/1937 | Grote | 424/234 |
| 3,584,129 | 6/1971 | Kitson | 424/234 |
| 3,629,412 | 12/1971 | Silber et al. | 424/232 |
| 4,264,582 | 4/1981 | Flora et al. | 424/234 |
| 4,282,214 | 8/1981 | Flora et al. | 424/234 |
| 4,282,216 | 8/1981 | Rovee et al. | 424/234 |

Primary Examiner—Stanley J. Friedman
Attorney, Agent, or Firm—Stiefel, Gross, Kurland & Pavane

[57] ABSTRACT

A pharmaceutical preparation for external use which comprises a solution of a non-steroid antipholgistic analgesic agent which is dissolved in at least one adjuvant selected from the group consisting of peppermint oil, methyl salicylate, ethyl salicylate and monoglycol salicylate in an amount at least sufficient to dissolve said antipholgistic analgesic agent, and bases for external use.

7 Claims, No Drawings

PHARMACEUTICAL PREPARATIONS

BACKGROUND OF THE INVENTION

1. Field of the Invention

The present invention relates to pharmaceutical preparations for external use. More specifically, it relates to preparations which are prepared by dissolving a non-steroid antiphlogistic analgesic agent in peppermint oil and/or a salicyclic acid ester and making the solution into a pharmaceutical form using a base for external use.

2. Description of the Prior Art

A great number of kinds are known as non-steroid antiphlogistic analgesic agents. Representative examples among those are ibuprofen, indomethacin, ketoprofen, flurbiprofen, suprofen, etc. The conventional pharmaceutical forms of these are orally administrable preparations and suppositories, and it is believed that any suitable form as a preparation for external use has not yet been known. Only one exception is a recent proposal on indomethacin being presented as an ointment comprising a mixture thereof with a glycol, a lower alcohol and water along with a gelling agent (see Japanese Patent Application Laid-open No. 81616/1978).

On the other hand, the non-steroid antiphlogistic analgesic agents, although being excellent in antiphlogistic or analgesic effect, sometimes exhibit drastic side effects upon the digestive organs in the case of the oral administration or on the rectum in the case of the suppository, and therefore, many investigations have been made in order to eliminate such a problem, but this has not been solved to this day.

The present inventor has discovered as the result of the intensive study that compounds which are non-steroid antiphlogistic analgesic agents and have an acetic acid or propionic acid group in the molecule are suprisingly capable of being readily soluble in such adjuvants as peppermint oil, salicyclic acid esters which exhibit pharmaceutical efficacy as such and that preparations for external use prepared using such solutions are extremely excellent as antiphlogistic or analgesic agents, thereby having accomplished the present invention.

The peppermint oil used in this invention has topical vasodilating effect, anticonvulsive effect, and used for external use in the form of an aqueous solution, poultice, plaster or the like or used as a topical stimulant for gargling (see Oleum Menthae Japonicae, Japanese Pharmacopeia and Peppermint, British Pharmacopeia). However, no example has been presented in which the peppermint oil is used as a solvent for antiphlogistic analgesic agents. Also, as for the salicylic acid esters used in this invention, there has been known no example where such are used as a solvent for antiphlogistic analgesic agents.

SUMMARY OF THE INVENTION

This invention provides a pharmaceutical preparation for external use which comprises a solution of a non-steroid compound which has an acetic acid or propionic acid group in the molecule and exerts antiphlogistic or analgesic effect which is dissolved in at least one adjuvant selected from the group consisting of peppermint oil, methyl salicylate, ethyl salicylate and monoglycol salicylate, along with a base for external use.

In this invention, the term "preparation for external use" means that used by applying to or plastering on the skin.

DESCRIPTION OF THE PREFERRED EMBODIMENTS

Examples of the non-steroid compound exerting antiphlogistic or analgesic effect which is used as an active ingredient in this invention [hereinafter referred to as Compound (I)] include compounds having a propionic acid group in the molecule, such as ibuprofen, ketoprofen, flurbiprofen, naproxen, benoxaprofen, pranoprofen, suprofen, fenoprofen, Y-9213 [2-{4-[2-imidazo-(1,2-a)-pyridyl]phenyl}propionic acid], tiaprofenic acid, protizinic acid etc., and compounds having an acetic acid group in the molecule, such as ibufenac, alclofenac, metiazinic acid, suxibuzone, oxepinac, sulindac, fentiazic, indomethacin, diclofenac, bendazac, zomepirac, tolmetin, fenbufen etc.

Each of the peppermint oil, methyl salicylate, ethyl salicylate and monoglycol salicylate used in this invention is that having pharmaceutical efficacy as such and moreover being capable of dissolving the aforesaid non-steroid antiphlogistic analgesic agent.

The peppermint oil is that containing l-menthol as a main ingredient, and although its composition varies to some extent depending on the kind of the plant source, any may be employed. In other words, this may be any peppermint oil included and defined in Japanese Pharmacopeia, British Pharmacopeia, West German Pharmacopeia etc.

According to this invention, it is preferred that Compound (I) is contained in an amount of 0.5-3.0% by weight as an active agent in the preparation for external use. Where the aforesaid adjuvant such as peppermint oil etc. is used solely as a dissolving agent, the amount just sufficient to dissolve Compound (I) may be satisfactory. Its minimum required amount is in general 1-10 parts by weight of peppermint oil, 5-16 parts by weight of methyl salicylate or ethyl salicylate, or 3-8 parts by weight of monoglycol salicylate per part by weight of Compound (I). This invention also includes a case where two or more kinds of these adjuvants are used so as to utilize these respective auxiliary pharmaceutical efficacies as agents for external use. In such a case, Compound (I) may be dissolved in one of the adjuvants, and thereafter desired amounts of the other adjuvant or adjuvants are added thereto. While Compound (I) is dissolved in these adjuvants, if the amount of a single adjuvant used is too much or the amount used is not sufficient for complete dissolution, it is advised to use two or more adjuvants to achieve dissolution, thus affording an effective adjuvant in which the features attributable to the respective adjuvants are versatile for the active ingredient. In general, it is preferred to employ at least peppermint oil. Its amount used where peppermint oil and salicylic acid ester are employed in combination is generally 3-16 parts by weight per part by weight of Compound (I).

Thus, according to this invention, one preferred preparation for external use contains 0.5-3.0% by weight of Compound (I) and appropriate amounts of the adjuvant and a base for external use.

Examples of the preferred form of the preparation for external use according to this invention include ointment, gel, gel cream, cream, poultice etc. The base for external use therefor may be chosen from the known ones. By way of illustration, examples of the gel base include a dilute aqueous carboxyvinyl polymer solution, an aqueous water-soluble basic substance (e.g. sodium hydroxide) solution etc. Using this base, the solution of Compound (I) dissolved in peppermint oil is made into a pharmaceutical form, thereby a gel preparation is readily obtained. The carboxyvinyl polymer herein used is a hydrophilic polymer obtained by polymerization using acrylic acid as a main component, and, for example, those commercially available under the trade names such as Carbopol 934, 940, 941 etc. from Goodrich Chemical Co., United States, and Hiviswako 103, 104, 105 etc. from Wako Junyaku Kogyo K.K., Japan may be employed.

The gel cream preparation includes that containing, in addition to the aforesaid gel base, an emulsifier (preferably a nonionic surfactant), and an oil component (e.g. liquid paraffin).

The cream base is, for example, a hydrophilic ointment (included in Japanese Pharmacopeia).

Examples of the poultice base include kaolin, glycerin, sodium acrylate, polyvinyl acetate, carboxyvinyl polymer etc.

Examples of the ointment base include lanolin, vaseline, beeswax, vegetable oil etc.

In addition to the above examples, it is possible to appropriately choose and employ bases for external use, preservatives and other additives known in the art. The conditions for preparing the preparation for external use may also be appropriately chosen and employed.

According to one aspect of the invention, it provides a method for preparing an antiphlogistic analgesic preparation for external use which comprises dissolving the non-steroid compound (I) in at least one adjuvant mentioned above in an amount at least sufficient for dissolving said compound (I) and then forming the resultant solution into a pharmaceutical preparation with the use of a base for external use.

In this invention, it is essential to dissolve Compound (I) in an adjuvant or adjuvants such as peppermint oil etc. beforehand. Once a solution has been made, addition of a base for external use which contains appropriate amounts of water, alcohol etc. will not cause separation of crystals of Compound (I), and thus a good preparation may be obtained. Since the peppermint oil has vasodilating effect, it is believed that Compound (I) is brought into contact with the skin while it is in solution in peppermint oil and hence the absorption thereof through the skin is promoted. In addition, refreshing feeling is offered by the peppermint oil on that occasion.

The methyl salicylate, ethyl salicylate and monoglycol salicylate have effects to promote the absorption of the active ingredient through the skin and to enhance the analgesic effect when used as a revulsive stimulant where the patient complains pain.

This invention is more particularly described by the following Examples and tests.

EXAMPLE 1

Cream preparations

The cream preparation having the below-mentioned components was prepared in the manner mentioned below.

| Components | w/w % |
|---|---|
| Flurbiprofen | 1.0 |
| Peppermint oil | 3.0 |
| Stearic acid | 5.0 |
| Cetanol | 5.0 |
| Liquid paraffin | 15.0 |
| White vaseline | 3.0 |
| Polyoxyethylenesorbitan monostearate | 2.0 |
| Sorbitan monostearate | 0.6 |
| Propyl p-oxybenzoate | 0.05 |
| Methyl p-oxybenzoate | 0.05 |
| Aqueous 10% triethanolamine | 3.5 |
| Sodium lauryl sulfate | 0.1 |
| Purified water | 61.7 |

Flurbiprofen was dissolved in peppermint oil, heating to about 70°–80° C. Stearic acid, cetanol, liquid paraffin, white vaseline, propyl p-oxybenzoate were added to the solution and heated to about 70°–80° C. to obtain an oil phase.

While, the mixture of methyl p-oxybenzoate, aqueous 10% triethanol amine, methyl p-oxybenzoate, triethanol amine solutions sodium lauryl sulfate and purified water was heated to 70°–80° C. on a water bath to obtain a solution.

The resulting solution was added in the above oil phase under sufficient stirring and cooled to give a cream preparation.

Similarly, the cream preparations having the components as shown in Table 1 were prepared, but when two or more adjuvants were used, the non-steroid antiphlogistic analgesic agent was dissolved in the mixture of the adjuvants prepared beforehand.

TABLE 1

| Component | (w/w %) | | | | | | | | | | | | | |
|---|---|---|---|---|---|---|---|---|---|---|---|---|---|---|
| Non-steroid agent | | | | | | | | | | | | | | |
| Flurbiprofen | 0.5 | 1.0 | 1.0 | 1.0 | 1.0 | 1.0 | 2.0 | 3.0 | 3.0 | | | | | |
| Ibuprofen | | | | | | | | | | 1.0 | 1.0 | 1.0 | 2.0 | 2.0 |
| Ketoprofen | | | | | | | | | | | | | | |
| Suprofen | | | | | | | | | | | | | | |
| Diclofenac | | | | | | | | | | | | | | |
| Indomethacin | | | | | | | | | | | | | | |
| Fentiazac | | | | | | | | | | | | | | |
| Adjuvant | | | | | | | | | | | | | | |
| Peppermint oil | 1.0 | 3.0 | | 2.0 | | | 8.0 | | 6.0 | 1.0 | | 6.0 | | 2.0 |
| Methyl salicylate | | | 12.0 | | 4.0 | 16.0 | | | | | | | | |
| Ethyl salicylate | | | | 4.0 | | | | | | | | | | |
| Monoglycol salicylate | | | | | 2.0 | | | 9.0 | 5.0 | | 5.0 | 10.0 | 6.0 | |
| Base | | | | | | | | | | | | | | |
| Stearic acid | 5.0 | 5.0 | 5.0 | 5.0 | 5.0 | 5.0 | 5.0 | 5.0 | 5.0 | 5.0 | 5.0 | 5.0 | 5.0 | 5.0 |
| Stearyl alcohol | | | | | | | | | | | | | | |
| Cetanol | 5.0 | 5.0 | 5.0 | 5.0 | 5.0 | 5.0 | 5.0 | 5.0 | 5.0 | 5.0 | 5.0 | 5.0 | 5.0 | 5.0 |
| Castor oil | | | | | | | | | | | | | | |

TABLE 1-continued

| Component | | | | | | | | | | | | | | |
|---|---|---|---|---|---|---|---|---|---|---|---|---|---|---|
| Isopropyl myristinate | | | | | | | | | 8.0 | | | | 10.0 | |
| Liquid paraffin | 15.0 | 15.0 | 15.0 | 15.0 | 15.0 | 15.0 | 15.0 | 15.0 | | 15.0 | 15.0 | 15.0 | | 15.0 |
| White vaseline | 3.0 | 3.0 | 3.0 | 3.0 | 3.0 | 3.0 | 3.0 | 3.0 | 3.0 | 3.0 | 3.0 | 3.0 | 5.0 | 3.0 |
| Polyoxyethylenesorbitan monostearate | 2.0 | 2.0 | 2.0 | 2.0 | 2.0 | 2.0 | 2.0 | 2.0 | 3.3 | 2.0 | 2.0 | 2.0 | 4.0 | 2.0 |
| Sorbitan monostearate | 0.6 | 0.6 | 0.6 | 0.6 | 0.6 | 0.6 | 0.6 | 0.6 | 1.0 | 0.6 | 0.6 | 0.6 | 1.2 | 0.6 |
| Propyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 |
| Methyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 |
| Aqueous 10% triethanol amine | 3.0 | 1.0 | 1.0 | 1.0 | 1.0 | 1.0 | 1.0 | 1.0 | | 3.0 | 1.0 | 1.0 | | 3.0 |
| Sodium lauryl sulfate | 0.1 | 0.1 | 0.1 | 0.1 | 0.1 | 0.1 | 0.1 | 0.1 | 0.1 | 0.1 | 0.1 | 0.1 | 0.1 | 0.1 |
| Purified water | 64.7 | 64.2 | 55.2 | 61.2 | 61.2 | 51.2 | 58.2 | 56.2 | 60.5 | 64.2 | 62.2 | 51.2 | 61.6 | 62.2 |

| Component | | | | | | | | | | | | | | |
|---|---|---|---|---|---|---|---|---|---|---|---|---|---|---|
| Non-steroid agent | | | | | | | | | | | | | | |
| Flurbiprofen | | | | | | | | | | | | | | |
| Ibuprofen | | | | | | | | | | | | | | |
| Ketoprofen | 1.0 | 1.0 | 1.0 | 1.0 | 2.0 | 2.0 | 3.0 | 3.0 | | | | | | |
| Suprofen | | | | | | | | | 0.5 | 0.5 | 1.0 | 1.0 | | |
| Diclofenac | | | | | | | | | | | | | 1.0 | 1.0 |
| Indomethacin | | | | | | | | | | | | | | |
| Fentiazac | | | | | | | | | | | | | | |
| Adjuvant | | | | | | | | | | | | | | |
| Peppermint oil | 1.0 | | | 2.0 | 4.0 | 2.0 | 7.0 | | | 2.0 | 8.0 | | 8.0 | |
| Methyl salicylate | | 5.0 | | | | | 5.0 | | | | | 10.0 | | |
| Ethyl salicylate | | | | | | | | | | | | | | |
| Monoglycol salicylate | | | 5.0 | 1.0 | | | | 9.0 | 1.5 | | | | | 5.0 |
| Base | | | | | | | | | | | | | | |
| Stearate acid | 5.0 | 5.0 | 5.0 | 5.0 | 5.0 | 5.0 | 5.0 | 5.0 | 5.0 | | | 5.0 | 5.0 | 5.0 |
| Stearyl alcohol | | | | | | | | | | 10.0 | 10.0 | | | |
| Cetanol | 5.0 | 5.0 | 5.0 | 5.0 | 5.0 | 5.0 | 5.0 | 5.0 | 5.0 | 5.0 | 5.0 | 5.0 | 5.0 | 5.0 |
| Castor oil | | | | | | | | | | | | | 15.0 | |
| Isopropyl myristinate | | | | | | | 8.0 | | | 15.0 | 15.0 | 10.0 | | |
| Liquid paraffin | 15.0 | 15.0 | 15.0 | 15.0 | 15.0 | 15.0 | | 15.0 | 15.0 | | | | | 10.0 |
| White vaseline | 3.0 | 3.0 | 3.0 | 3.0 | 3.0 | 3.0 | 3.0 | 3.0 | 3.0 | 5.0 | 5.0 | 5.0 | 3.0 | 3.0 |
| Polyoxyethylenesorbitan monostearate | 2.0 | 2.0 | 2.0 | 2.0 | 2.0 | 2.0 | 3.3 | 2.0 | 2.0 | 4.0 | 4.0 | 4.0 | 2.0 | 2.0 |
| Sorbitan monostearate | 0.6 | 0.6 | 0.6 | 0.6 | 0.6 | 0.6 | 1.0 | 0.6 | 0.6 | 1.2 | 1.2 | 1.2 | 0.6 | 0.6 |
| Propyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 |
| Methyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 |
| Aqueous 10% triethanol amine | 3.0 | 1.0 | 1.0 | 1.0 | 3.0 | 3.0 | | 1.0 | 1.0 | 2.0 | 2.0 | | 1.0 | 1.0 |
| Sodium lauryl sulfate | 0.1 | 0.1 | 0.1 | 0.1 | 0.1 | 0.1 | 0.1 | 0.1 | 0.1 | 0.2 | 0.2 | 0.1 | 0.1 | 0.1 |
| Purified water | 64.2 | 62.2 | 62.2 | 64.2 | 60.2 | 62.2 | 59.5 | 56.2 | 66.2 | 55.0 | 48.5 | 58.6 | 59.2 | 67.2 |

| Component | | | | | | | | | | | | | | |
|---|---|---|---|---|---|---|---|---|---|---|---|---|---|---|
| Non-steroid agent | | | | | | | | | | | | | | |
| Flurbiprofen | | | | | | | | | | | | | | |
| Ibuprofen | | | | | | | | | | | | | | |
| Ketoprofen | | | | | | | | | | | | | | |
| Suprofen | | | | | | | | | | | | | | |
| Diclofenac | 1.0 | 1.0 | 1.0 | 1.0 | | | | | | | | | | |
| Indomethacin | | | | | 0.5 | 0.5 | 0.5 | 1.0 | 1.0 | 1.0 | 1.0 | 1.0 | 3.0 | |
| Fentiazac | | | | | | | | | | | | | | 0.5 | 1.0 |
| Adjuvant | | | | | | | | | | | | | | |
| Peppermint oil | 8.0 | | 10.0 | 5.0 | 2.0 | | 3.0 | 8.0 | 8.0 | | 4.0 | 6.0 | | 2.5 |
| Methyl salicylate | 8.0 | 10.0 | | | | | 5.0 | | | | | 8.0 | | 16.0 |
| Ethyl salicylate | | | | | | | | | 16.0 | | | | | |
| Monoglycol salicylate | | | 8.0 | | 1.5 | | | | | | 3.0 | | 15.0 | |
| Base | | | | | | | | | | | | | | |
| Stearic acid | 5.0 | 5.0 | 5.0 | 5.0 | | 5.0 | 5.0 | 10.0 | | 5.0 | 5.0 | 5.0 | 5.0 | 5.0 | 5.0 |
| Stearyl alcohol | | | | | 10.0 | | | | 10.0 | | | | | |
| Cetanol | 5.0 | 5.0 | 5.0 | 5.0 | 5.0 | 5.0 | 5.0 | 5.0 | 5.0 | 5.0 | 5.0 | 5.0 | 5.0 | 5.0 |
| Castor oil | | | | | | 15.0 | | | | | | | | |
| Isopropyl myristinate | | 15.0 | 10.0 | | 15.0 | | 15.0 | 15.0 | 10.0 | 8.0 | 10.0 | 15.0 | | |
| Liquid paraffin | 15.0 | | | 15.0 | | 15.0 | | | | | | | 10.0 | 10.0 |
| White vaseline | 3.0 | 3.0 | 3.0 | 3.0 | 5.0 | 3.0 | 3.0 | 5.0 | 5.0 | 3.0 | 3.0 | 3.0 | 3.0 | 3.0 |
| Polyoxyethylenesorbitan monostearate | 2.0 | 2.0 | 2.0 | 2.0 | 4.0 | 2.0 | 2.0 | 4.0 | 4.0 | 4.0 | 3.3 | 4.0 | 4.0 | 2.0 | 2.0 |
| Sorbitan monostearate | 0.6 | 0.6 | 0.6 | 0.6 | 1.2 | 0.6 | 0.6 | 1.2 | 1.2 | 1.2 | 1.0 | 1.2 | 1.2 | 0.6 | 0.6 |
| Propyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Methyl p-oxybenzoate | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Aqueous 10% triethanol amine | 1.0 | 1.0 | 1.0 | 1.0 | 2.0 | 1.0 | 1.0 | 2.0 | 2.0 | 1.0 | | 1.0 | 1.0 | 1.0 | 1.0 |
| Sodium lauryl sulfate | 0.1 | 0.1 | 0.1 | 0.1 | 0.2 | 0.1 | 0.1 | 0.2 | 0.2 | 0.2 | 0.1 | 0.2 | 0.2 | 0.1 | 0.1 |
| Purified water | 51.2 | 57.2 | 62.2 | 54.2 | 55.0 | 66.2 | 59.7 | 48.5 | 48.5 | 53.5 | 66.5 | 55.5 | 47.5 | 70.2 | 56.2 |

EXAMPLE 2

Gel cream preparations

The gel cream preparation having the below-mentioned components was prepared in the manner mentioned below.

| Components | w/w % |
|---|---|
| Fluribiprofen | 0.5 |
| Peppermint oil | 1.0 |
| Liquid paraffin | 20.0 |
| Lauromacrogol | 1.0 |
| Aqueous 4% carboxyvinylpolymer (Carbopol 940) | 25.0 |
| Aqueous 2% NaOH | 20.0 |
| Aqueous 1% EDTA.2 Na | 2.0 |
| Purified water | 30.5 |

Flurbiprofen was dissolved in peppermint oil, heating to about 70°–80° C. To this solution was added liquid paraffin and lauromacrogol, which was heated to about 70°–80° C. on a water bath.

While, an aqueous 1% EDTA.2Na (disodium ethylenediamine tetraacetate) solution and purified water were stirred in an aqueous 4% carboxyvinylpolymer solution, to which 2% sodium hydroxide was added and heated to 70°–80° C. on a water bath. To the resulting mixture was the above flurbiprofen solution under well stirring. The mixture was cooled to obtain a gel cream which shows pH 6.36 (at 25° C.) and 34,000 cp of viscosity.

Similarly, the gel cream preparations shown in Table 2 were prepared, but when two or more adjuvants were used, they were beforehand mixed and used to dissolve the non-steroid agent.

TABLE 2

| Component | (w/w %) | | | | | | | | | | | | | | | | | |
|---|---|---|---|---|---|---|---|---|---|---|---|---|---|---|---|---|---|---|
| Non-steroid agent | | | | | | | | | | | | | | | | | | |
| Flurbiprofen | 0.5b* | 0.5 | 1.0 | 1.0 | 1.0 | 1.0 | 1.0 | 1.0a* | 2.0 | 3.0 | 3.0 | | | | | | | |
| Ibuprofen | | | | | | | | | | | | 0.5 | 1.0 | 1.0 | 1.0 | 2.0c* | 3.0 | |
| Ketoprofen | | | | | | | | | | | | | | | | | | |
| Suprofen | | | | | | | | | | | | | | | | | | |
| Diclofenac | | | | | | | | | | | | | | | | | | |
| Indomethacin | | | | | | | | | | | | | | | | | | |
| Fentiazac | | | | | | | | | | | | | | | | | | |
| Adjuvant | | | | | | | | | | | | | | | | | | |
| Peppermint oil | 1.0 | | 8.0 | | | | | 3.0 | 8.0 | 6.0 | 6.0 | 3.0 | 2.0 | 1.0 | 2.0 | 3.0 | 6.0 | |
| Methyl salicylate | | 6.0 | | | 5.0 | 12.0 | 4.0 | | | | 12.0 | 2.0 | | | 4.0 | | | |
| Ethyl salicylate | | | | | | | | | | | | | | | | | | |
| Monoglycol salicylate | | | | 3.0 | | | 2.0 | | | 3.0 | | | | | | | | |
| Base | | | | | | | | | | | | | | | | | | |
| Liquid paraffin | | | 10.0 | | | | | 10.0 | 10.0 | | | 10.0 | 10.0 | 10.0 | | 20.0 | | |
| Isopropyl myristinate | 3.5 | 20.0 | | 10.0 | 20.0 | 10.0 | 10.0 | | | 10.0 | 10.0 | | | | 20.0 | | 10.0 | |
| Castor oil | | | | | | | | | | | | | | | | | | |
| Lauromacrogol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | |
| Aqueous 4% Carbopol 940 | 25.0 | 20.0 | 25.0 | 25.0 | 25.0 | 25.0 | 25.0 | 25.0 | 25.0 | 25.0 | 25.0 | 25.0 | 25.0 | 25.0 | 20.0 | 25.0 | 25.0 | |
| Aqueous 2% NaOH | 20.0 | 16.0 | 20.0 | 10.0 | 10.0 | 10.0 | 10.0 | 20.0 | 20.0 | 10.0 | 10.0 | 10.0 | 20.0 | 20.0 | 16.0 | 20.0 | 10.0 | |
| Aqueous 1% EDTA.2Na | 2.0 | | 2.0 | 2.0 | 2.0 | 2.0 | 2.0 | 2.0 | 2.0 | 2.0 | 2.0 | 2.0 | 2.0 | 2.0 | | 2.0 | 2.0 | |
| Purified water | 47.0 | 36.5 | 48.0 | 48.0 | 36.0 | 39.0 | 45.0 | 38.0 | 32.0 | 40.0 | 31.0 | 46.5 | 39.0 | 40.0 | 31.0 | 27.0 | 43.0 | |
| White vaseline | | | | | | | | | | | | | | | 5.0 | | | |

| Component | (w/w %) | | | | | | | | | | | | | | | | |
|---|---|---|---|---|---|---|---|---|---|---|---|---|---|---|---|---|---|
| Non-steroid agent | | | | | | | | | | | | | | | | | |
| Flurbiprofen | | | | | | | | | | | | | | | | | |
| Ibuprofen | | | | | | | | | | | | | | | | | |
| Ketoprofen | 0.5 | 1.0 | 1.0 | 1.0 | 1.0 | 2.0 | 2.0 | 3.0 | | | | | | | | | |
| Suprofen | | | | | | | | | 0.5 | 1.0 | 1.0 | 1.0 | 1.0 | 2.0 | 3.0 | | |
| Diclofenac | | | | | | | | | | | | | | | | 0.5 | 1.0 |
| Indomethacin | | | | | | | | | | | | | | | | | |
| Fentiazac | | | | | | | | | | | | | | | | | |
| Adjuvant | | | | | | | | | | | | | | | | | |
| Peppermint oil | | | 10.0 | 8.0 | 2.0 | 3.5 | | 3.0 | 3.0 | 8.0 | 2.0 | | 1.0 | 8.0 | | 1.0 | |
| Methyl salicylate | | 5.0 | 6.0 | | 2.0 | | | | | | | 5.0 | | | | | 5.0 |
| Ethyl salicylate | | | | | | | | | | | | | | | | | |
| Monoglycol salicylate | 4.0 | | | | | 6.0 | 6.0 | | | | | | 2.0 | 7.0 | 15.0 | | |
| Base | | | | | | | | | | | | | | | | | |
| Liquid paraffin | 10.0 | | | | | 20.0 | | | | | | | | | | | |
| Isopropyl myristinate | | 10.0 | 5.0 | 10.0 | 10.0 | | 20.0 | 10.0 | 20.0 | 20.0 | 20.0 | 20.0 | 20.0 | 20.0 | 10.0 | 20.0 | 20.0 |
| Castor oil | | | | | | | | | | | | | | | | | |
| Lauromacrogol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.5 | 1.5 |
| Aqueous 4% Carbopol 940 | 25.0 | 25.0 | 25.0 | 25.0 | 25.0 | 25.0 | 20.0 | 25.0 | 25.0 | 25.0 | 25.0 | 25.0 | 25.0 | 20.0 | 25.0 | 40.0 | 40.0 |
| Aqueous 2% NaOH | 10.0 | 10.0 | 10.0 | 10.0 | 10.0 | 20.0 | 16.0 | 10.0 | 20.0 | 20.0 | 10.0 | 10.0 | 10.0 | 16.0 | 10.0 | 15.0 | 15.0 |
| Aqueous 1% EDTA.2Na | 2.0 | 2.0 | 2.0 | 2.0 | 2.0 | 2.0 | | 2.0 | 2.0 | 2.0 | 2.0 | 2.0 | 2.0 | | 2.0 | 2.0 | 2.0 |
| Purified water | 47.5 | 46.0 | 40.0 | 43.0 | 47.0 | 26.5 | 35.0 | 40.0 | 28.5 | 23.0 | 39.0 | 36.0 | 38.0 | 21.0 | 34.0 | 20.0 | 15.5 |
| White vaseline | | | | | | | | | | | | | | 5.0 | | | |

| Component | (w/w %) |
|---|---|

TABLE 2-continued

| Non-steroid agent | | | | | | | | | | | | | | | | | |
|---|---|---|---|---|---|---|---|---|---|---|---|---|---|---|---|---|---|
| Flurbiprofen | | | | | | | | | | | | | | | | | |
| Ibuprofen | | | | | | | | | | | | | | | | | |
| Ketoprofen | | | | | | | | | | | | | | | | | |
| Suprofen | | | | | | | | | | | | | | | | | |
| Diclofenac | 1.0 | 1.0 | 1.0 | 1.0 | 2.0 | | | | | | | | | | | | |
| Indomethacin | | | | | | 0.5 | 1.0 | 1.0 | 3.0 | 0.5 | 0.5 | 1.0 | 1.0 | | | | |
| Fentiazac | | | | | | | | | | | | | | 1.0 | 1.0 | 1.0 | 1.0 |
| Adjuvant | | | | | | | | | | | | | | | | | |
| Peppermint oil | 2.0 | | 10.0 | 8.0 | 10.0 | | 1.0 | 2.0 | 15.0 | 3.0 | 3.0 | | 8.0 | 2.0 | 2.0 | | |
| Methyl salicylate | | | | 8.0 | | | | | | | 5.0 | | | | | 5.0 | |
| Ethyl salicylate | | | | | 2.5 | | | | | | | 15.0 | | | | | |
| Monoglycol salicylate | 1.0 | 3.0 | | | 16.0 | | 2.0 | | 9.0 | | | | 5.0 | | 1.0 | | 3.0 |
| Base | | | | | | | | | | | | | | | | | |
| Liquid paraffin | | | | | | | | | | | | | | | | | |
| Isopropyl myristinate | | | 10.0 | 10.0 | 5.0 | | | | 10.0 | 20.0 | 20.0 | 20.0 | 20.0 | 20.0 | 20.0 | 20.0 | 20.0 |
| Castor oil | 20.0 | 20.0 | | | | 20.0 | 20.0 | 20.0 | | | | | | | | | |
| Lauromacrogol | 1.5 | 1.5 | 1.0 | 1.0 | 1.0 | 1.5 | 1.5 | 1.5 | 1.0 | 1.0 | 1.0 | 1.0 | 1.0 | 1.0 | 1.0 | 1.0 | 1.0 |
| Aqueous 4% Carbopol 940 | 40.0 | 40.0 | 25.0 | 25.0 | 25.0 | 40.0 | 40.0 | 40.0 | 25.0 | 25.0 | 20.0 | 25.0 | 25.0 | 25.0 | 40.0 | 40.0 | 40.0 |
| Aqueous 2% NaOH | 15.0 | 15.0 | 10.0 | 10.0 | 10.0 | 15.0 | 15.0 | 15.0 | 12.0 | 20.0 | 16.0 | 12.0 | 12.0 | 20.0 | 15.0 | 15.0 | 15.0 |
| Aqueous 1% EDTA.2Na | 2.0 | 2.0 | 2.0 | 2.0 | 2.0 | 2.0 | 2.0 | 2.0 | 2.0 | 2.0 | | 2.0 | 2.0 | 2.0 | 2.0 | 2.0 | 2.0 |
| Purified water | 17.5 | 17.5 | 41.0 | 35.0 | 29.0 | 18.5 | 17.5 | 18.5 | 23.0 | 28.5 | 34.5 | 24.0 | 34.0 | 23.0 | 19.0 | 18.0 | 16.0 |
| White vaseline | | | | | | | | | | | | | | | | | |

*a pH (at 28.0° C.) 6.33, Viscosity (cp) 34,000
b pH (at 25.5° C.) 6.35, Viscosity (cp) 31,000
c pH (at 26.0° C.) 6.28, Viscosity (cp) 34,000

EXAMPLE 3

Gel preparation

The gel preparation having the blow-mentioned components was prepared in the manner mentioned below.

| Components | w/w % |
|---|---|
| Fluribiprofen | 0.5 |
| Peppermint oil | 1.5 |
| Aqueous 4% carboxyvinyl-polymer (Carbopol 940) | 30.0 |
| Aqueous 2% NaOH | 24.0 |
| Purified water | 44.0 |

Flurbiprofen was dissolved in peppermint oil, heating to about 70°–80° C.

While, to an aqueous 4% carboxyvinylpolymer solution was slowly added an aqueous 2% sodium hydroxide and then purified water, under well stirring. The above flurbiprofen solution was added to the mixture and continued to stir until a homogeneous solution is obtained. The preparation shows pH 6.54 (at 28° C.) and 45,000 cp of viscosity.

Further the gel preparations having the components which are shown in Table 3 were prepared in the same manner as above mentioned, but when two or more adjuvants were used, the non-steroid agent was dissolved in the mixture of the adjuvants prepared beforehand.

TABLE 3

| Component | (w/w %) | | | | | | | | | | | | |
|---|---|---|---|---|---|---|---|---|---|---|---|---|---|
| Non-steroid agent | | | | | | | | | | | | | |
| Flubiprofen | 1.0 | 1.0 | 1.0 | 1.0e* | 1.0 | 1.0 | 2.0 | 3.0 | | | | | |
| Ibuprofen | | | | | | | | | 0.5d* | 1.0 | 1.0 | 1.0 | 2.0 |
| Ketoprofen | | | | | | | | | | | | | |
| Suprofen | | | | | | | | | | | | | |
| Diclofenac | | | | | | | | | | | | | |
| Indomethacin | | | | | | | | | | | | | |
| Fentiazac | | | | | | | | | | | | | |
| Adjuvant | | | | | | | | | | | | | |
| Peppermint oil | | | 1.0 | 3.0 | 2.0 | | 6.0 | 3.0 | 1.0 | | | 2.0 | 4.0 |
| Methyl salicylate | | 12.0 | | | 4.0 | 4.0 | | | | 16.0 | | | |
| Ethyl salicylate | | | | | | | | | | | | | |
| Monoglycol salicylate | 8.0 | | 2.0 | | | 2.0 | | 6.0 | | | 8.0 | | |
| Base | | | | | | | | | | | | | |
| Aqueous 4% Carbopol 940 | 30.0 | 30.0 | 30.0 | 30.0 | 30.0 | 30.0 | 30.0 | 30.0 | 35.0 | 30.0 | 30.0 | 35.0 | 35.0 |
| Aqueous 2% NaOH | 24.0 | 15.0 | 15.0 | 24.0 | 15.0 | 15.0 | 24.0 | 15.0 | 28.0 | 15.0 | 15.0 | 28.0 | 28.0 |
| Purified water | 37.0 | 42.0 | 51.0 | 42.0 | 48.0 | 48.0 | 38.0 | 43.0 | 35.5 | 38.0 | 46.0 | 34.0 | 31.0 |

| Component | (w/w %) | | | | | | | | | | | |
|---|---|---|---|---|---|---|---|---|---|---|---|---|
| Non-steroid agent | | | | | | | | | | | | |
| Flurbiprofen | | | | | | | | | | | | |
| Ibuprofen | 2.0 | | | | | | | | | | | |
| Ketoprofen | | 0.5 | 0.5 | 1.0 | 1.0 | 1.0 | 1.0 | 1.0 | 2.0 | 3.0 | | |
| Suprofen | | | | | | | | | | | 0.5 | 1.0 | 1.0 |
| Diclofenac | | | | | | | | | | | | |

TABLE 3-continued

| Component | | | | | | | | | | | | | (w/w %) |
|---|---|---|---|---|---|---|---|---|---|---|---|---|---|
| Indomethacin | | | | | | | | | | | | | |
| Fentiazac | | | | | | | | | | | | | |
| Adjuvant | | | | | | | | | | | | | |
| Peppermint oil | 3.0 | | 2.0 | | | 2.0 | | 3.0 | 6.0 | 3.0 | 4.0 | 8.0 | |
| Methyl salicylate | | 8.0 | | | 5.0 | 2.0 | | | | | | | |
| Ethyl salicylate | | | | | | | | | | | | | |
| Monoglycol salicylate | 3.0 | | | 3.0 | | | 3.0 | | | 6.0 | | | 8.0 |
| Base | | | | | | | | | | | | | |
| Aqueous 4% Carbopol 940 | 30.0 | 30.0 | 35.0 | 35.0 | 30.0 | 30.0 | 30.0 | 35.0 | 35.0 | 30.0 | 35.0 | 35.0 | 30.0 |
| Aqueous 2% NaOH | 24.0 | 15.0 | 28.0 | 28.0 | 24.0 | 15.0 | 15.0 | 28.0 | 28.0 | 15.0 | 28.0 | 28.0 | 15.0 |
| Purified water | 38.0 | 46.5 | 34.5 | 33.0 | 40.0 | 50.0 | 51.0 | 33.0 | 29.0 | 43.0 | 32.5 | 28.0 | 46.0 |

| Component | | | | | | | | | | | | | (w/w %) |
|---|---|---|---|---|---|---|---|---|---|---|---|---|---|
| Non-steroid agent | | | | | | | | | | | | | |
| Flurbiprofen | | | | | | | | | | | | | |
| Ibuprofen | | | | | | | | | | | | | |
| Ketoprofen | | | | | | | | | | | | | |
| Suprofen | 2.0 | | | | | | | | | | | | |
| Diclofenac | | 1.0 | 1.0 | 1.0 | 1.0 | | | | | | | | |
| Indomethacin | | | | | | 0.5 | 0.5f* | 1.0 | 1.0 | 1.0 | 3.0 | | |
| Fentiazac | | | | | | | | | | | | 0.5 | 1.0 |
| Adjuvant | | | | | | | | | | | | | |
| Peppermint oil | 10.0 | 10.0 | 8.0 | 5.0 | | 8.0 | 6.0 | 6.0 | | | 15.0 | 4.0 | 10.0 |
| Methyl salicylate | 10.0 | | 8.0 | | | | | 8.0 | | 15.0 | | | |
| Ethyl salicylate | | | | | | | | | | | | | |
| Monoglycol salicylate | | | | 8.0 | 8.0 | | | | 6.0 | | 9.0 | | 6.0 |
| Base | | | | | | | | | | | | | |
| Aqueous 4% Carbopol 940 | 30.0 | 30.0 | 30.0 | 30.0 | 30.0 | 35.0 | 35.0 | 30.0 | 30.0 | 30.0 | 30.0 | 30.0 | 30.0 |
| Aqueous 2% NaOH | 24.0 | 15.0 | 15.0 | 15.0 | 15.0 | 28.0 | 28.0 | 15.0 | 24.0 | 15.0 | 15.0 | 15.0 | 15.0 |
| Purified water | 24.0 | 44.0 | 38.0 | 41.0 | 46.0 | 28.5 | 30.5 | 40.0 | 39.0 | 39.0 | 28.0 | 50.5 | 38.0 |

*d pH (at 28.0° C.) 6.41, Viscosity (cp) 52,000
f pH (at 30.8° C.) 6.75, Viscosity (cp) 46,000

EXAMPLE 4

Poultice preparations

The poultice preparations having the below-mentioned components was prepared in the manner mentioned below.

| Components | w/w % |
|---|---|
| Flurbiprofen | 1.0 |
| Peppermint oil | 3.0 |
| Methyl salicylate | 50.8 |
| Kaolin finely shifted | 45.0 |

| Components | w/w % |
|---|---|
| Concentrated glycerin | 0.2 |

Flurbiprofen was dissolved in the mixture of peppermint oil and methyl salicylate, heating to about 70°–80° C. Concentrated glycerin which was heated was mixed with a fine kaolin dried at 110° C. To the resulting mixture which was cooled was added the above flurbiprofen solution under sufficient stirring, to obtain the homogeneous preparation.

Similarly the poultice preparations having the components which are shown in Table 4 were prepared.

TABLE 4

| Component | | | | | | | | | | | | | | | (w/w %) |
|---|---|---|---|---|---|---|---|---|---|---|---|---|---|---|---|
| Non-steroid agent | | | | | | | | | | | | | | | |
| Flurbiprofen | 1.0 | 1.0 | 1.0 | 1.0 | 2.0 | 2.0 | 3.0 | | | | | | | | |
| Ibuprofen | | | | | | | | 1.0 | 1.0 | | | | | | |
| Ketoprofen | | | | | | | | | | 1.0 | 1.0 | 1.0 | 2.0 | 3.0 | |
| Suprofen | | | | | | | | | | | | | | | 1.0 |
| Diclofenac | | | | | | | | | | | | | | | |
| Indomethacin | | | | | | | | | | | | | | | |
| Fentiazac | | | | | | | | | | | | | | | |
| Adjuvant | | | | | | | | | | | | | | | |
| Peppermint oil | | 3.0 | | 6.0 | 5.0 | 5.0 | 3.0 | | 8.0 | | 2.0 | | 3.0 | 3.0 | |
| Methyl salicylate | | 0.2 | | | | 5.0 | | 5.0 | | | | 5.0 | | | 16.0 |
| Ethyl salicylate | | | 12.0 | 10.0 | 5.0 | | | | | 10.0 | 3.0 | | | | |
| Monoglycol salicylate | 3.0 | | | | | | 6.0 | | | | | | 3.0 | 6.0 | |
| Base | | | | | | | | | | | | | | | |
| Kaolin finely sifted | 55.0 | 50.8 | 50.0 | 45.0 | 50.0 | 50.0 | 52.0 | 54.0 | 50.0 | 50.0 | 55.0 | 55.0 | 52.0 | 52.0 | 45.0 |
| Concentrated glycerine | 41.0 | 45.0 | 37.0 | 38.0 | 38.0 | 38.0 | 36.0 | 40.0 | 41.0 | 39.0 | 39.0 | 39.0 | 40.0 | 36.0 | 38.0 |

| Component | | | | | | (w/w %) |
|---|---|---|---|---|---|---|
| Non-steroid agent | | | | | | |
| Flurbiprofen | | | | | | |
| Ibuprofen | | | | | | |
| Ketoprofen | | | | | | |
| Suprofen | 1.0 | 1.0 | | | | |
| Diclofenac | | | 1.0 | 1.0 | 1.0 | 3.0 |

TABLE 4-continued

| | | | | | | | | | | | | | | | |
|---|---|---|---|---|---|---|---|---|---|---|---|---|---|---|---|
| Indomethacin | | | | | | 0.5 | 0.5 | 1.0 | 1.0 | 3.0 | 3.0 | 3.0 | | | |
| Fentiazac | | | | | | | | | | | | | 1.0 | 3.0 | |
| Adjuvant | | | | | | | | | | | | | | | |
| Peppermint oil | 6.0 | | 10.0 | 8.0 | | 15.0 | | | 10.0 | | | 18.0 | 15.0 | | 10.0 |
| Methyl salicylate | 10.0 | | | 8.0 | 16.0 | | | 8.0 | | | | | | | |
| Ethyl salicylate | | | | | | | 8.0 | | | | | 24.0 | | | |
| Monoglycol salicylate | | 5.0 | | | | 24.0 | | | | 8.0 | 15.0 | | 9.0 | 8.0 | 15.0 |
| Base | | | | | | | | | | | | | | | |
| Kaolin finely sifted | 45.0 | 54.0 | 55.0 | 50.0 | 50.0 | 35.0 | 52.0 | 52.0 | 55.0 | 50.0 | 50.0 | 35.0 | 45.0 | 50.0 | 40.0 |
| Concentrated glycerine | 38.0 | 40.0 | 34.0 | 33.0 | 33.0 | 23.0 | 39.5 | 39.5 | 34.0 | 41.0 | 32.0 | 20.0 | 28.0 | 41.0 | 32.0 |

Stability test of the preparations

A representative gel cream preparation of flurbiprofen (1.0%) (marked with (a) in Table 2) or gel preparation of ibuprofen (0.5%) (marked with (d) in Table 3) was subjected to the stability test. The preparation was stood for a maximum 90 days at a temperature of 40°, 50° or 60° C. and the non-steroid active agent was measured by the use of a high pressure liquid chromatograph (Shimadzu Corp. of Japan, SPD-2A, LC-3A). The results are shown in Tables 5 and 6. Further, the above mentioned preparations were not observed on any change of the dosage form and decomposition of the active agent after standing for 90 days at room temperature.

TABLE 5

| | The fluribiprofen (1%) gel cream (a) in Example 2 | |
|---|---|---|
| Period (day) | Temperature (°C.) | Ratio of fluribiprofen detected to fluribiprofen added in the preparation (%) |
| 0 | | 100.2 |
| 30 | 40 | 100.4 |
| | 50 | 100.4 |
| | 60 | 100.3 |
| 60 | 40 | 100.0 |
| | 50 | 100.3 |
| | 60 | 99.8 |
| 90 | 40 | 100.1 |
| | 50 | 100.1 |
| | 60 | 100.0 |

TABLE 6

| | The ibuprofen (0.5%) gel preparation (d) in Example 4 | |
|---|---|---|
| Period (day) | Temperature (°C.) | Ratio of ibuprofen detected to ibuprofen added in the preparation (%) |
| 0 | | 99.7 |
| 30 | 40 | 99.8 |
| | 50 | 100.0 |
| | 60 | 100.0 |
| 60 | 40 | 99.9 |
| | 50 | 100.1 |
| | 60 | 99.8 |

TABLE 6-continued

| | The ibuprofen (0.5%) gel preparation (d) in Example 4 | |
|---|---|---|
| Period (day) | Temperature (°C.) | Ratio of ibuprofen detected to ibuprofen added in the preparation (%) |
| 90 | 40 | 100.0 |
| | 50 | 99.8 |
| | 60 | 99.7 |

Pharmacological tests

1. Inhibitory effect on UV-erythema

One group consisted of three male guinea pigs weighing 280–380 g, whose hair (5 × 5 cm$^2$) at the right side of abdomen was sheared and shaved by electric clippers and electric razor.

The test preparation (50 mg) was applied to the resulting hairless skin in a size of 4 cm diameter, with rubbing and the applied area was covered with paper and gum tape. After standing for an hour, the covering was removed and the applied test preparation was also wiped off by warm water. Then, the three parts (each diameter of 7 mm) in the applied skin were irradiated by ultraviolet rays (an artificial sunlight of 600W provided by Amako Ika Ltd. of Japan) for 90 seconds. After 2 hours of the irradiation, an extent of UV-erythema was evaluated, in reference of the standard having no irradiation.

0: no change
1: slightly reddish
2: apparent erythema with a clear border
3: strong erythema with a clear border The results are shown in Table 7.

2. Inhibitory effect on carrageenin edema

One group consisted of three male rats weighing 195–240 g. The test preparation was well applied to the skin of sole of left hind leg, which was covered. After standing for an hour, 0.1 ml of 1% carrageenin physiologic saline solution was subcutaneously injected into the sole. After 4 hours of the injection, a volume of edema was measured to calculate inhibition ratio.

The results are shown in Table 7.

TABLE 7

| Preparation | Concentration of active ingredient (%) | UV-erythema inhibitory effect (50 mg application) | | Carrageenin edema inhibitory effect (50 mg application) | |
|---|---|---|---|---|---|
| | | Mean score ± S.E. | inhibition ratio (%) | Mean volume of edema ± S.E. (ml) | inhibition ratio (%) |
| No application | — | 1.7 ± 0.37 | — | 0.55 ± 0.04 | — |
| Reference gel preparation | 1.0 | 0.4 ± 0.18** | 76.5 | 0.45 ± 0.01 | 18.2 |
| Flurbiprofen gel preparation (e in Table 3) | base alone 1.0 | 1.3 ± 0.17 0.6 ± 0.18** | 23.5 64.7 | 0.65 ± 0.05 0.31 ± 0.05** | 18.2 43.6 |

TABLE 7-continued

| | | | | | |
|---|---|---|---|---|---|
| Flurbiprofen gel | base alone | 1.1 ± 0.18 | 17.6 | 0.51 ± 0.05 | 7.3 |
| cream preparation | 1.0 | 0.9 ± 0.20** | 47.1 | 0.25 ± 0.08** | 54.5 |
| (a in Table 2) | | | | | |

Note
(1) **means that the preparation has significant difference from "no application" at $P < 0.01$ by t-test
(2) Reference gel cream preparation:

| | |
|---|---|
| Hiviswako 104 | 1.0 g |
| (Wako Junyaku K.K.,Japan) | |
| Indomethacin | 1.0 g |
| Propylene glycol | 10.0 g |
| Ethanol | 40.0 g |
| Diisopropanol amine | 1.1 g |
| Purified water | 47.9 g |

CONSIDERATION

With respect to UV-erythema, both of the preparations of the invention and the reference gel preparation showed significantly high inhibitory effect, compared with no application case.

On the other hand, the preparations of the invention showed significantly high in hibitory effect on carrageenin edema in comparison with no application case. However the reference gel preparation did not show any significant difference from no application case.

It is found that the preparations of the invention are well absorbed in the deep subcutaneous part to exert their own pharmacological activities, in addition to curing an inflammation at the skin surface.

What is claimed is:

1. A pharmaceutical preparation for external use comprising a solution of from about 0.5 to about 3.0% by weight of a non-steroid compound wherein the non-steroid compound is ibuprofen, ketoprofen, flurbiprofen, naproxen, benoxaprofen, fenoprofen, ibufenac, alclofenac, diclofenac, tiaprofenic acid, fentiazac or fenbufen, the non-steroid compound being dissolved in at least one adjuvant selected from the group consisting of peppermint oil, methyl salicylate, ethyl salicylate and monoglycol salicylate in an amount of from 1 to 16 parts of the adjuvant per part of the non-steroid compound, and a base for external use.

2. A pharmaceutical preparation according to claim 1 wherein the ratio by weight of peppermint oil to the non-steroid compound is 1–10 parts:1 part.

3. A pharmaceutical preparation according to claim 2 wherein the ratio by weight of peppermint oil to the non-steroid compound is 2–8 parts:1 part.

4. A pharmaceutical preparation according to claim 1 wherein the ratio by weight of methyl salicylate or ethyl salicylate to the non-steroid compound is 5–16 parts:1 part.

5. A pharmaceutical preparation according to claim 1 wherein the ratio by weight of monoglycol salicylate to the non-steroid compound is 3–8 parts:1 part.

6. A pharmaceutical preparation according to claim 1 wherein the ratio by weight of peppermint oil and one selected from the group consisting of methyl salicylate, ethyl salicylate and monoglycol salicylate to the non-steroid compound is 3–16 parts:1 part.

7. A pharmaceutical preparation according to claim 1 which is in a gel, gel cream, cream or poultice form.

* * * * *